United States Patent
Convent et al.

(10) Patent No.: US 9,658,154 B2
(45) Date of Patent: May 23, 2017

(54) SPECTROMETER AND GAS ANALYZER

(71) Applicant: SICK AG, Waldkirch/Breisgau (DE)

(72) Inventors: Jurgen Convent, Waldkirch (DE); Torsten Trick, Kenzingen (DE); Andreas Bonisch, Gundelfingen (DE)

(73) Assignee: SICK AG, Waldkirch/Breisgau (DE)

( * ) Notice: Subject to any disclaimer, the term of this patent is extended or adjusted under 35 U.S.C. 154(b) by 0 days.

(21) Appl. No.: 15/157,709

(22) Filed: May 18, 2016

(65) Prior Publication Data
US 2016/0341659 A1    Nov. 24, 2016

(30) Foreign Application Priority Data
May 20, 2015    (DE) .................. 10 2015 107 942

(51) Int. Cl.
G01J 3/28        (2006.01)
G01N 21/33       (2006.01)
G01J 3/02        (2006.01)
G01J 3/18        (2006.01)
(Continued)

(52) U.S. Cl.
CPC ............ *G01N 21/33* (2013.01); *G01J 3/0205* (2013.01); *G01J 3/18* (2013.01); *G01J 3/427* (2013.01); *G01N 21/31* (2013.01)

(58) Field of Classification Search
CPC ........ G01J 3/02; G01J 3/18; G01J 3/28; G01J 3/427; G01J 3/2803; G01J 3/2823; G01N 21/33
See application file for complete search history.

(56) References Cited

U.S. PATENT DOCUMENTS

| 5,644,396 A * | 7/1997 | Hopkins, II ............ G01J 3/02 356/301 |
| 6,842,250 B2 | 1/2005 | Schwarz |

(Continued)

FOREIGN PATENT DOCUMENTS

| DE | 3736201 C2 | 12/1993 |
| DE | 4433193 A1 | 3/1996 |

(Continued)

*Primary Examiner* — Abdullahi Nur
(74) *Attorney, Agent, or Firm* — Nath, Goldberg & Meyer; Jerald L. Meyer

(57) ABSTRACT

A spectrometer has an entry aperture for coupling in electromagnetic radiation to be spectroscope, a refractive or diffractive optical element arranged such that electromagnetic radiation which is coupled in through the entry aperture is incident on the refractive or diffractive optical element to be spectrally split there, and at least two individual detectors which, for the detection of different spectral ranges of the split electromagnetic radiation, are arranged next to one another in the direction of the spectral splitting of the electromagnetic radiation. Electromagnetic radiation from a predetermined ultraviolet wavelength range is directed onto one of the individual detectors by the optical element and electromagnetic radiation from a predetermined blue wavelength range is directed onto another of the detectors by the optical element. Electromagnetic radiation from the intermediate wavelength range between the predetermined ultraviolet wavelength range and the predetermined blue wavelength range are not detected.

26 Claims, 1 Drawing Sheet

(51) Int. Cl.
*G01J 3/427* (2006.01)
*G01N 21/31* (2006.01)

(56) References Cited

U.S. PATENT DOCUMENTS

| | | | |
|---|---|---|---|
| 7,403,286 B2 * | 7/2008 | Kato | ................. G01J 3/02 356/328 |
| 7,876,435 B2 | 1/2011 | Becker-Ross et al. | |
| 2007/0103679 A1 * | 5/2007 | Yoo | ................. G01J 3/02 356/301 |
| 2011/0255075 A1 | 10/2011 | Kerstan et al. | |
| 2014/0078492 A1 | 3/2014 | Silny | |

FOREIGN PATENT DOCUMENTS

| | | |
|---|---|---|
| DE | 4223211 C2 | 3/1999 |
| DE | 19916072 A1 | 10/2000 |
| DE | 10137428 A1 | 2/2003 |
| DE | 10055905 B4 | 5/2004 |
| DE | 10121499 B4 | 8/2007 |
| DE | 19543729 B4 | 8/2008 |
| DE | 19962779 B4 | 6/2009 |
| DE | 102008054056 A1 | 5/2010 |
| DE | 102010047061 A1 | 4/2012 |
| DE | 102012007609 A1 | 10/2013 |
| EP | 0121404 B1 | 5/1989 |

* cited by examiner

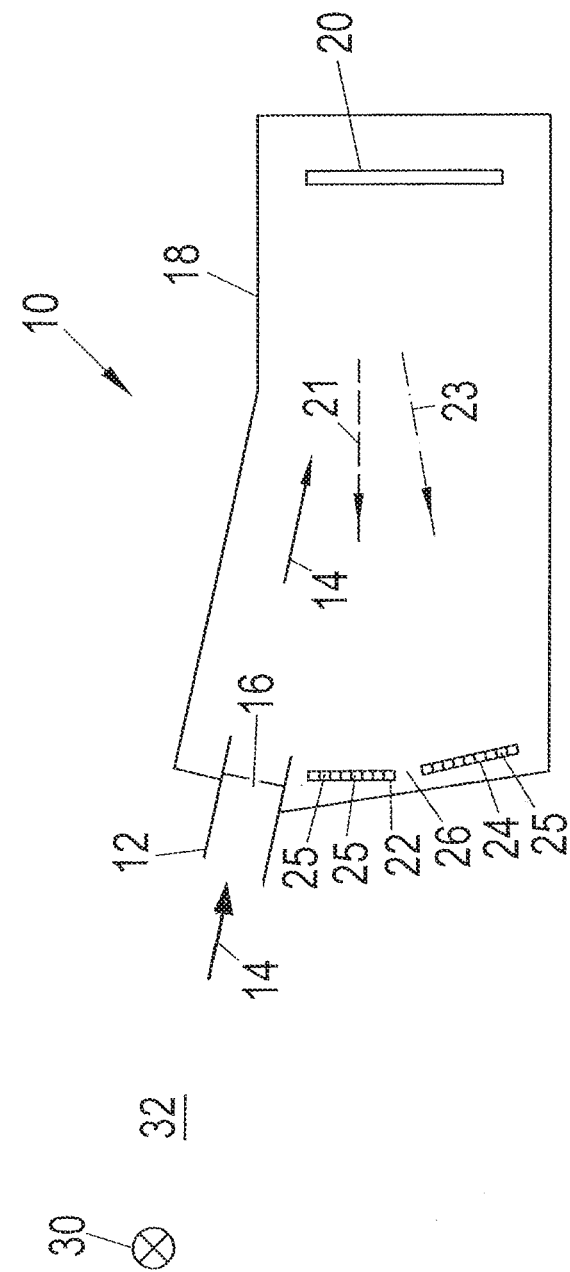

SPECTROMETER AND GAS ANALYZER

The present invention relates to a spectrometer having an entry aperture for coupling in electromagnetic radiation to be spectroscoped and having a refractive optical element or a diffractive optical element which is arranged such that electromagnetic radiation coupled in through the entry aperture is incident on the refractive or diffractive optical element in order to be spectrally split there.

The invention further relates to a gas analyzer having such a spectrometer and to a method of determining the presence and/or the concentration of one or more gas components.

Spectrometers are used, for example, in gas analyzers to determine the concentration or presence of various gases within an optical measurement path. For this purpose, light is sent through an optical measurement path in which the measurement gases or measurement gas components are to be detected and/or their concentration is to be determined. The term "light" is used in the present text for electromagnetic radiation in general and optionally also comprises the infrared or ultraviolet wavelength range.

In such a gas analyzer, the measurement light irradiates the optical measurement path in a manner known per se and is in this respect absorbed in dependence on the wavelength by the respective gas components present. The light is incident on the entry aperture of the spectrometer after this wavelength-dependent absorption and is incident from there, for example, on a diffraction grating at which it is differently diffracted in dependence on the wavelength. The light thus diffracted in dependence on the wavelength is imaged onto a detector, with the position of the point of incidence depending on the wavelength. A spectrum results in this respect in a manner known per se from which it can be read which wavelengths have been absorbed more or less in order thus to be able to draw a conclusion on the presence and/or concentration of individual gas components. The term "gas" is also used here for the individual gas components which may be present together in the optical measurement path.

Detector arrays are used as detectors, for example, in which a plurality of photodiodes are arranged next to one another on a component in the direction of the spectral splitting by the diffraction grating. Alternatively, elongated PSD (position-sensitive device) elements can also be used as detector arrays.

So-called flat-field gratings are frequently used as diffraction gratings, i.e. flat gratings which are calculated for a specific wavelength and for exactly defined spectrometer geometries. A use of such a grating outside its specification, which is possible, for example, by use of a longer detector array (which can also detect light which is outside the wavelength range specified for the diffraction grating) or a use outside the specified wavelength range can have the result that the ideal imaging is no longer disposed in a detector plane, but rather on a sphere. The detector array would consequently have to have a spherical curvature.

Gases which frequently have to be measured in process and emission monitoring as well as in tunnel air monitoring are, for example, NO, $SO_2$, $NH_3$ and $NO_2$. These gases inter alia absorb in a spectral range between approximately 190 nm and approximately 250 nm.

However, $NO_2$, for example, has to be measured in very small concentrations in a tunnel in tunnel monitoring, which is, on the other hand, most easily possible in a spectral range around 450 nm. With higher demands on the $NO_2$ measurement accuracy in process monitoring or in the addressed tunnel monitoring, it is necessary to move to the absorption range around 450 nm for the $NO_2$ measurement. This can be problematic in that such a measurement is not compatible with a measurement in the ultraviolet range up to 190 nm (in which the other named gases can also easily be detected) since typical ultraviolet spectrometers do not support this wide spectral range for the above-named reasons. In addition, there is a wide spectral range in which no information can or has to be evaluated between the relevant spectral ranges between 190 nm and 250 nm, on the one hand, and the range around 450 nm, on the other hand.

To be able to examine the different wavelength ranges, a plurality of gratings are, for example, used in known spectrometers. DE 10 37 428 A1, for instance, describes a spatially separate arrangement of two detectors in which some of the light in the plane of the first detector is incident on a further diffraction grating through a cut-out and is subsequently detected by a second detector array.

US 2014/00784921 A1 describes the use of a plurality of diffraction gratings for different wavelength ranges.

Other known arrangements use movable detectors whose position or alignment within the spectrometer can be varied such that they detect the respective spectral range of interest of the diffracted light. This requires complex and/or expensive, mechanically movable and therefore potentially more fragile parts.

DE 10 201 0 047 061 A1 describes a spectrometer having a diffraction grating for the spectral splitting of the incident electromagnetic radiation. Two partly overlapping detectors serve for the recording of two overlapping spectral ranges.

A spectrometer having a diffraction grating is known from DE 10 201 2 007 609 A1, wherein two detectors arranged at a right angle are provided for different overlapping wavelength ranges, with the light being divided by a beam splitter for the two detectors.

DE 10 2008 054 056 A1 describes a spectrometric arrangement having a diffraction grating which images light diffracted in dependence on wavelength onto a detector. A reference detector serves for the recording of another order of diffraction.

EP 0 121 404 B1 describes a spectrometric gas analyzer having a detector.

It is the object of the invention to provide a spectrometer, a gas analyzer and a method of gas analysis which allow an inexpensive and simple implementation.

This object is satisfied by a spectrometer having the features of claim 1, by a gas analyzer having the features of claim 10 and by a method having the features of claim 11. Advantageous embodiments are the subject of dependent claims.

A spectrometer in accordance with the invention has an entry aperture (light coupling aperture), in particular an entry gap. Said entry aperture serves for coupling in electromagnetic radiation to be spectroscoped. The spectrometer in accordance with the invention additionally has a refractive optical element or a diffractive optical element which is arranged such that electromagnetic radiation which is coupled in through the entry aperture is incident thereon to be split spectrally there. At least two individual detectors are located in the optical path of the split electromagnetic radiation and are arranged next to one another in the direction of the spectral splitting of the electromagnetic radiation. The serve for the detection of different spectral ranges of the split electromagnetic radiation.

The individual detectors are in a known manner, for example, detector arrays (e.g. CMOS, NMOS, CCD arrays or CCD fields, scintillator coatings, PSD elements or similar) which also extend at least in the direction of the spectral splitting. The individual detectors are arranged next to one another in the direction of the spectral splitting. In this manner, small detector elements, that is in particular short detector arrays, can be used which can be manufactured inexpensively and are available inexpensively.

It is additionally possible through the use of individual detectors for different spectral ranges that different technologies are used for the detectors which are particularly suitable for the respective spectral range to be detected (that is, for example, in particular the above-named different detector technologies). In addition, the read-out times or other process parameters for the different individual detectors can, for example, be selected differently in order to be able ideally to determine the respective spectral ranges to be detected by the individual detectors.

The wavelength-dependent splitting of the light coupled into the spectrometer can take place, for example, using a refractive optical element (for example, a prism) or a diffractive optical element (for example, a diffraction grating).

It is in particular possible with the solution in accordance with the invention to use a relatively simply designed diffractive optical element which can likewise be manufactured inexpensively and simply. It can, for example, be a single diffraction grating, preferably a planar grating having a constant grating constant.

With a spectrometer in accordance with the invention, one of the detectors is arranged such that electromagnetic radiation from a predetermined ultraviolet wavelength range is directed onto it by the refractive or diffractive optical element and a second detector is arranged such that electromagnetic radiation from a predetermined blue wavelength range is directed onto it by the refractive or diffractive optical element. Electromagnetic radiation from the intermediate wavelength range between the predetermined ultraviolet wavelength range and the predetermined blue wavelength range is not detected.

In the spectrometer in accordance with the invention, the at least two individual detectors are therefore arranged such that they do not detect any light having a wavelength from a spectral range not of interest.

In a particularly advantageous embodiment, the at least two individual detectors are arranged spaced apart from one another in the direction of the spectral splitting for this purpose such that electromagnetic radiation in a predetermined spectral range is not incident on one of these detectors after its interaction with the refractive or diffractive optical element. The spacing is in this respect based on the wavelength range to be omitted and on the geometry of the spectrometer.

A wavelength region not of interest can in this way be omitted in a further cost-saving manner such that the evaluation becomes simpler and less expensive.

This is in particular of advantage, for example, on the use of a spectrometer in accordance with the invention for gas analysis in process and emission monitoring and in tunnel air monitoring. The gases NO, $SO_2$, $NH_3$ and $NO_2$ which frequently have to be detected in this respect can admittedly be detected, for example, in a spectral range between approximately 190 nm and approximately 250 nm. However, a high measurement accuracy is in particular desirable with the critical gas $NO_2$ in the process sector or it must be possible, e.g. in tunnels, to detect it in very small concentrations. This is, however, particularly favorably possible in the range around 450 nm due to the absorption properties of the $NO_2$. If it is therefore desired simultaneously to evaluate the range between approximately 190 nm and approximately 250 nm, on the one hand, and the range around 450 nm, on the other hand, in the gas analysis, a large wavelength range therebetween is not of any interest.

In an advantageous embodiment, provision is alternatively or additionally made that the at least two individual detectors are arranged tilted at an angle with respect to one another. In this manner, the circumstance can be taken into account that, for example, when using a single planar diffraction grating, the focusing or the resolution is no longer as good in the marginal ranges of the spectral range in accordance with the specification of the grating. Such aberrations can be compensated by a correspondingly selected mutual tilt of the at least two detectors with respect to one another.

The tilt angle is, for example, between 10° and 20°, for example at approximately 15°.

As stated, a spectrometer in accordance with the invention can in particular advantageously be used with a gas analyzer such as is the subject matter of claim 10.

Such a gas analyzer has a spectrometer in accordance with the invention. In addition, a light source is provided, wherein an optical measurement path is located between the light source and the entry gap of the spectrometer, in which measurement path absorption may take place by a measurement gas or by a plurality of measurement gases. Light from the light source passes through the optical measurement path where the absorption by the measured gas or measured gases dependent on the wavelength may take place, with the absorption being able to be measured by the spectrometer in dependence on the wavelength.

The advantages of such a gas analyzer in accordance with the invention and the special embodiments and advantageous uses result from the advantages and embodiments named above for the spectrometer in accordance with the invention.

The gases to be spectroscoped which are in the optical measurement path can e.g. be process gas which is branched off from a process to be analyzed with the gas analyzer. In other applications, the optical measurement path, for example, passes transversely through a flue gas chimney to detect the absorption taking place therein. The optical measurement path can, for example, also be a free path within a tunnel in which the concentration of specific pollutants are to be measured.

The light source can be a single light source which transmits a wide spectrum so that a plurality of absorption lines of the absorption spectrum to be expected can be detected. It can in this respect, for example, be a xenon flash lamp or a xenon high-pressure lamp. The light source is selected in dependence on the absorption spectrum to be expected. It can, on the other hand, also comprise a plurality of single light sources which each cover an individual spectral range particularly well. Combinations of deuterium lamps and halogen lamps or of deuterium lamps and light-emitting diodes of corresponding wavelength characteristics can thus be used, for example, to be able to examine different spectral ranges with sufficient light intensity. If a plurality of single light sources are used, their light is coupled into the optical measurement path either simultaneously or consecutively.

The invention also relates to a method of determining the presence and/or the concentration of one or more gases having such a gas analyzer in accordance with the invention. In this respect, the absorption taking place in the optical measurement path of the gas analyzer is determined in a spectrally resolved manner by the spectrometer of the gas analyzer and a conclusion is drawn from the absorption spectrum on the presence and/or concentration of one or more gases.

The advantages of such a method in accordance with the invention and the special embodiments and advantageous uses result from properties named above for the spectrometer in accordance with the invention.

The invention will be explained with reference to the FIGURE in the following. There is shown The FIGURE in a schematic illustration not to scale a gas analyzer in accordance with the invention with a spectrometer in accordance with the invention.

The spectrometer 10 comprises a spectrometer housing 18. The spectrometer housing has a light entry aperture 12 through which light 14 (as a rule from the ultraviolet, visible and/or infrared spectral ranges) can enter into the spectrometer housing 18, with it passing through an entry gap 16. For this purpose, a light source 30 is located at the other side of an optical measurement path 32 in which the gas to be analyzed is located whose absorption properties are to be measured with the aid of the spectrometer 10.

A diffraction grating 20 is located in the spectrometer housing 18 and is illuminated by light 14 which enters into the spectrometer housing 18 through the entry gap 16.

The diffraction grating 20 is a planar grating structure of a constant grating constant. Light of different wavelengths is diffracted in a manner known per se at different angles at the planar grating structure 20 according to the laws of light diffraction. With the spectrometer shown, this is done at the grating 20 in reflection geometry.

A different angle is in this respect adopted for the diffracted light in dependence on the wavelength of the light incident on the diffracting grating 20. The diffracted light beams 21, 23 of two different wavelengths are indicated by way of example. Individual detectors 22 and 24 are acted on by light of different spectral ranges in this respect.

The individual detectors 22 and 24 are detector arrays in which a plurality of photodiodes 25 are arranged next to one another, only indicated here, in each case in the direction of the spectral splitting by the diffraction grating 20 (that is in the direction of the extent of the detector array) in order, for example, to form a CCD array which extends in the direction of the spectral splitting of the diffracted light (that is here the FIGURE plane). These detectors are connected in a manner not shown to an evaluation unit which reads out the photodiodes to determine the intensity of the light incident at the respective point in order thus to determine which component of the light transmitted by the light source 30 has been absorbed more or less in the optical measurement path 32.

In the arrangement shown in the FIGURE, the two detectors 22 and 24 are arranged spaced apart from one another such that they can detect different spectral ranges of the light diffracted at the diffraction grating 20. An intermediate region 26 in which no detection can take place is located therebetween. The arrangement of the spectrometer is selected in this respect in dependence on the wavelengths to be detected such that the absorption of light of a wavelength which is diffracted into the region 26 is of no interest or is of secondary interest for the corresponding application.

On the use of the spectrometer 10 for the gas analysis in, for example, process monitoring or emission monitoring as well as in tunnel air monitoring, the spectral range is, for example, in particular of interest between approximately 190 nm and approximately 250 nm in which absorption by the gases NO, $SO_2$, $NH_3$ and $NO_2$ can be detected when such gases are in the optical measurement path 32. On the other hand, a different absorption line in the range of 450 nm can provide a very exact conclusion on the presence and/or concentration, in particular of the particularly critical gas $NO_2$.

One of the detectors 22, 24 is accordingly arranged such that it can measure the spectral range between 190 nm and 250 nm, while the other detector is arranged such that it can measure the range around 450 nm (that is, for example, a range from 430 nm to 460 nm). Wavelengths therebetween (that is in the described example between 250 nm and 430 nm) are diffracted by the diffraction grating 20 into the region 26 and are not detected. This is also not necessary because the named relevant gases do not absorb in a detectable manner or in an easily detectable manner in this spectral range.

The detectors 22 and 24 in the embodiment shown are arranged at an angle with respect to one another which is spanned in the plane in which the light is split by the diffraction grating 20. This plane corresponds to the shown FIGURE plane. Aberrations, in particular in the marginal regions of the spectral ranges, can be compensated by this tilt. The angle amounts to 15°, for example.

The embodiment shown comprises a diffraction grating 20 which is designed as a reflection grating. In an embodiment which is not shown, a transmission grating can also be provided, with then the detectors 22, 24 being located behind the diffraction grating in the direction of radiation of the incident light 14.

The gas analyzer shown in the FIGURE has a spectrometer in accordance with the invention. In addition, a light source 30 is provided, wherein an optical measurement path 32 is located between the light source and the entry aperture 12 of the spectrometer 10, in which measurement path absorption may take place by a measurement gas or by a plurality of measurement gases. Light 14 from the light source 30 passes through the optical measurement path 32 where the absorption dependent on the wavelength may take place by the measurement gas or measurement gases, with the absorption being able to be measured by the spectrometer 10 in dependence on the wavelength.

A conclusion can then be drawn on the presence and/or concentration of the measurement gas components in the optical measurement path 32 from the absorption spectrum thus determined.

The gas to be spectroscoped which is not in the optical measurement path 32 can e.g. be a process gas which is branched off from a process to be analyzed with the gas analyzer. The optical measurement path can, for example, also be a free path within a tunnel in which the concentrations of specific pollutants are to be measured.

The combination of a deuterium lamp (which easily covers the range from approximately 190 nm to 250 nm) with a halogen lamp (which covers the range around 450 nm particularly well) can, for example, be used as a light source 30 for the detection of the named gases NO, $SO_2$, $NH_3$ and $NO_2$ in the described manner.

Differing from the above description, provision can also be made, for example, that the optical measurement path is run through twice. For this purpose, the light of the light source is sent through the optical measurement path to a reflector which directs the light back through the optical measurement path again to the spectrometer. In this manner, the light source and the spectrometer are arranged on the same side of the optical measurement path and can, for example, be arranged in a common housing.

REFERENCE NUMERAL LIST 10 spectrometer
12 light entry aperture 14 entering light
16 entry gap
18 spectrometer housing
20 diffraction grating
21 diffracted light
22 detector
23 diffracted light
24 detector
25 photodiode
26 detector-free region
30 light source
32 optical measurement path

The invention claimed is:

1. A spectrometer for gas analysis in tunnel air monitoring, the spectrometer having an entry aperture for coupling in electromagnetic radiation to be spectroscoped; having a refractive or diffractive optical element which is arranged such that electromagnetic radiation which is coupled in through the entry aperture is incident on the refractive or diffractive optical element to be spectrally split there; and having at least two individual detectors which are located in the optical paths thereof for the detection of different spectral ranges of the split electromagnetic radiation,
  wherein the at least two individual detectors are arranged next to one another in the direction of the spectral splitting of the electromagnetic radiation; and
  wherein one of the at least two individual detectors is arranged such that electromagnetic radiation from an ultraviolet wavelength range between 190 nm and 250 nm is deflected onto it by the refractive or diffractive optical element and another one of the at least two individual detectors is arranged such that electromagnetic radiation from a blue wavelength range between 410 nm and 460 nm is deflected onto it by the refractive or diffractive optical element;
  with electromagnetic radiation from the intermediate wavelength range between the said ultraviolet wavelength range and the said blue wavelength range not being detected.

2. The spectrometer in accordance with claim 1, wherein the entry aperture is an entry gap.

3. The spectrometer in accordance with claim 1, wherein the optical element for the spectral splitting is a diffractive optical element.

4. The spectrometer in accordance with claim 3, wherein the diffractive optical element is a diffraction grating.

5. The spectrometer in accordance with claim 4, wherein the diffraction grating is a planar grating with a constant grating constant.

6. The spectrometer in accordance with claim 1, wherein the at least two individual detectors are arranged spaced apart from one another in the direction of the spectral splitting such that electromagnetic radiation in a predetermined spectral range is not incident on one of the detectors.

7. The spectrometer in accordance with claim 1, wherein the at least two individual detectors are based on different detector technologies.

8. The spectrometer in accordance with claim 1, wherein the at least two individual detectors are arranged at an angle with respect to one another which is spanned in the plane of the spectral splitting.

9. A gas analyzer having a spectrometer in accordance with claim 1 in which the entry aperture is an entry gap; having a light source; and having an optical measurement path arranged between the light source and the entry gap of the spectrometer for gas or gases to be examined spectrally using the gas analyzer.

10. A method of determining the presence and/or concentration of one or more gases using a gas analyzer in accordance with claim 9, the method comprising the steps of:
  determining the absorption taking place in the optical measurement path of the gas analyzer in a spectrally resolved manner by the spectrometer of the gas analyzer and determining at least one of the presence and the concentration of one or more gases from the absorption spectrum.

11. The method in accordance with claim 10, wherein the gases whose presence and/or concentration is to be determined in the optical measurement path comprise NO, $SO_2$, $NH_3$ and/or $NO_2$.

12. The method in accordance with claim 10, wherein the operating parameters of the at least two individual detectors are selected differently on the operation of the gas analyzer.

13. The method in accordance with claim 10, wherein the read-out times of the at least two individual detectors are selected differently on the operation of the gas analyzer.

14. A spectrometer having an entry aperture for coupling in electromagnetic radiation to be spectroscoped; having a refractive or diffractive optical element which is arranged such that electromagnetic radiation which is coupled in through the entry aperture is incident on the refractive or diffractive optical element to be spectrally split there; and having at least two individual detectors which are located in the optical paths thereof for the detection of different spectral ranges of the split electromagnetic radiation,
  wherein the at least two individual detectors are arranged next to one another in the direction of the spectral splitting of the electromagnetic radiation; and
  wherein one of the at least two individual detectors is arranged such that electromagnetic radiation from a predetermined ultraviolet wavelength range is deflected onto it by the refractive or diffractive optical element and another one of the at least two individual detectors is arranged such that electromagnetic radiation from a predetermined blue wavelength range is deflected onto it by the refractive or diffractive optical element;
  with electromagnetic radiation from the intermediate wavelength range between the predetermined ultraviolet wavelength range and the predetermined blue wavelength range not being detected; and
  wherein the at least two individual detectors are based on different detector technologies.

15. The spectrometer in accordance with claim 14, wherein the entry aperture is an entry gap.

16. The spectrometer in accordance with claim 14, wherein the optical element for the spectral splitting is a diffractive optical element.

17. The spectrometer in accordance with claim 16, wherein the diffractive optical element is a diffraction grating.

18. The spectrometer in accordance with claim 17, wherein the diffraction grating is a planar grating with a constant grating constant.

19. The spectrometer in accordance with claim 14, wherein the at least two individual detectors are arranged spaced apart from one another in the direction of the spectral splitting such that electromagnetic radiation in a predetermined spectral range is not incident on one of the detectors.

20. The spectrometer in accordance with claim 14, wherein the at least two individual detectors are arranged at an angle with respect to one another which is spanned in the plane of the spectral splitting.

21. A gas analyzer having a spectrometer in accordance with claim 14 in which the entry aperture is an entry gap; having a light source; and having an optical measurement path arranged between the light source and the entry gap of the spectrometer for gas or gases to be examined spectrally using the gas analyzer.

22. A method of determining the presence and/or concentration of one or more gases using a gas analyzer in accordance with claim 21, the method comprising the steps of:
   determining the absorption taking place in the optical measurement path of the gas analyzer in a spectrally resolved manner by the spectrometer of the gas analyzer and determining at least one of the presence and the concentration of one or more gases from the absorption spectrum.

23. The method in accordance with claim 22, wherein the gases whose presence and/or concentration is to be determined in the optical measurement path comprise NO, $SO_2$, $NH_3$ and/or $NO_2$.

24. The method in accordance with claim 22, wherein the operating parameters of the at least two individual detectors are selected differently on the operation of the gas analyzer.

25. The method in accordance with claim 22, wherein the read-out times of the at least two individual detectors are selected differently on the operation of the gas analyzer.

26. The spectrometer in accordance with claim 14, wherein one of the at least two individual detectors is arranged such that electromagnetic radiation from a range between 190 nm and 250 nm is deflected onto it by the refractive or diffractive optical element; and wherein the other one of the at least two individual detectors is arranged such that electromagnetic radiation from a range between 410 nm and 460 nm is deflected onto it by the refractive or diffractive optical element, with electromagnetic radiation from the intermediate wavelength range between these wavelengths not being detected.

* * * * *